United States Patent
Curry et al.

(10) Patent No.: US 12,280,165 B2
(45) Date of Patent: Apr. 22, 2025

(54) DISINFECTING DEVICE

(71) Applicant: JC Technologies LLC, Auburn, AL (US)

(72) Inventors: John Edgar Curry, Auburn, AL (US); Harry Edmar Schulz, Auburn, AL (US)

(73) Assignee: JC Technologies LLC, Auburn, AL (US)

( * ) Notice: Subject to any disclaimer, the term of this patent is extended or adjusted under 35 U.S.C. 154(b) by 888 days.

(21) Appl. No.: 17/467,536

(22) Filed: Sep. 7, 2021

(65) Prior Publication Data

US 2021/0393826 A1     Dec. 23, 2021

Related U.S. Application Data

(63) Continuation of application No. 17/151,562, filed on Jan. 18, 2021, now Pat. No. 11,110,189, which is a continuation-in-part of application No. 16/900,243, filed on Jun. 12, 2020, now Pat. No. 10,894,101.

(51) Int. Cl.
    *A61L 2/10*     (2006.01)
    *H05K 7/20*     (2006.01)

(52) U.S. Cl.
    CPC ............ *A61L 2/10* (2013.01); *H05K 7/20254* (2013.01); *H05K 7/20272* (2013.01); *A61L 2202/11* (2013.01); *A61L 2202/26* (2013.01)

(58) Field of Classification Search
    CPC ....................................................... A61L 2/10
    See application file for complete search history.

(56) References Cited

U.S. PATENT DOCUMENTS

| | | | | |
|---|---|---|---|---|
| 3,619,336 A | * | 11/1971 | Hughes | ..................... D04H 1/52 |
| | | | | 428/102 |
| 6,596,016 B1 | * | 7/2003 | Vreman | ............... A61N 5/0621 |
| | | | | 128/903 |
| 8,651,704 B1 | | 2/2014 | Gordin et al. | |
| 9,603,960 B2 | | 3/2017 | Dobrinsky et al. | |
| 10,894,101 B1 | | 1/2021 | Curry et al. | |

(Continued)

FOREIGN PATENT DOCUMENTS

| | | |
|---|---|---|
| CN | 104413807 A | 3/2015 |
| CN | 220068910 U | 11/2023 |

(Continued)

OTHER PUBLICATIONS

International Search Report and Written Opinion dated Feb. 22, 2024 cited in Application No. PCT/US23/73834, 11 pgs.

(Continued)

*Primary Examiner* — Donald R Spamer
(74) *Attorney, Agent, or Firm* — BEKIARES ELIEZER LLP

(57) ABSTRACT

The present disclosure provides a device comprising: at least one opening, the at least one opening being configured receive an object; an inner cavity within the at least one opening, the inner cavity comprising: a light emitting diode (LED), a heat sink connecting the LED to a thermal reservoir, and an insulating layer arranged on the thermal reservoir, the insulating layer comprising an orifice arranged over the LED such that light from the LED passes through the orifice of the insulating layer; and a power source configured to power the LED.

20 Claims, 13 Drawing Sheets

(56) References Cited

U.S. PATENT DOCUMENTS

| | | |
|---|---|---|
| 11,110,189 B1 | 9/2021 | Curry et al. |
| 2002/0146343 A1 | 10/2002 | Jenkins et al. |
| 2007/0008149 A1 | 1/2007 | Bolling |
| 2007/0139930 A1* | 6/2007 | Spivak .................. A61N 5/0616 |
| | | 362/294 |
| 2009/0222072 A1 | 9/2009 | Robinson et al. |
| 2010/0024100 A1 | 2/2010 | Sokolowski et al. |
| 2011/0243789 A1 | 10/2011 | Roberts |
| 2013/0220297 A1 | 8/2013 | Sivucka et al. |
| 2015/0165228 A1 | 6/2015 | Lemens et al. |
| 2015/0257249 A1 | 9/2015 | Kim |
| 2016/0114067 A1 | 4/2016 | Dobrinsky et al. |
| 2016/0317687 A1* | 11/2016 | Dayton ..................... A61L 2/10 |
| 2017/0128742 A1 | 5/2017 | Rabiner et al. |
| 2017/0136136 A1 | 5/2017 | Li et al. |
| 2017/0246466 A1 | 8/2017 | Murphy et al. |
| 2018/0104367 A1 | 4/2018 | Bettles et al. |
| 2020/0139152 A1* | 5/2020 | Behler .................. A61N 5/0621 |
| 2020/0261611 A1 | 8/2020 | Bonutti et al. |
| 2023/0001031 A1 | 1/2023 | Curry et al. |

FOREIGN PATENT DOCUMENTS

| | | |
|---|---|---|
| WO | 2007010255 A1 | 1/2007 |
| WO | 2017207636 A1 | 12/2017 |
| WO | 2024059492 A2 | 3/2024 |

OTHER PUBLICATIONS

PCT Application No. PCT/US21/13837 filed Jan. 18, 2021 entitled "Disinfecting Device", Inventors: John Edgar Curry et al.
International Search Report and Written Opinion dated Apr. 8, 2021 cited in Application No. PCT/US21/13837, 13 pgs.
European Extended Search Report dated Jun. 27, 2024 cited in Application No. 21822093.7, 9 pgs.

* cited by examiner

DISINFECTING DEVICE

RELATED APPLICATIONS

This application is a Continuation of U.S. application Ser. No. 17/151,562 filed on Jan. 18, 2021, which issues on Sep. 7, 2021 as U.S. Pat. No. 11,110,189, which is a Continuation-In-Part of U.S. application Ser. No. 16/900,243 filed Jun. 12, 2020, which issued on Jan. 19, 2021 as U.S. Pat. No. 10,894,101, which are incorporated herein by reference in its entirety.

It is intended that the above-referenced application may be applicable to the concepts and embodiments disclosed herein, even if such concepts and embodiments are disclosed in the referenced applications with different limitations and configurations and described using different examples and terminology.

FIELD OF DISCLOSURE

The present disclosure relates to disinfecting surfaces, and more specifically, to disinfecting surfaces of hands.

BACKGROUND

Disinfecting hands is one of the most effective ways to avoid spreading contagious diseases. There are many methods used, to disinfect hands such as, soap and water, waterless soap, or solvent-based hand sanitizer. Each of these methods have disadvantages. For example, the use of soap and water is done at a fixed fixture such as a sink or hand washing station, the use of solvent-based hand sanitizers may be problematic since they are quickly depleted, and may not be available under some conditions.

A quick, effective, easily portable, and convenient device for sanitizing hands is desired. This need and other needs are satisfied by the various aspects of the present disclosure.

SUMMARY

In accordance with the purposes of the present disclosure, as embodied and broadly described herein, the present disclosure, in one aspect, relates to devices, garments, and methods for disinfecting surfaces, such as, for example, skin surfaces. In another aspect, the present disclosure relates to a device of the present disclosure can include a device comprising: at least one opening, the at least one opening being configured receive an object; the inner cavity within the at least one opening, the inner cavity comprising: a light emitting diode (LED), a heat sink connecting the LED to the thermal reservoir, and an insulating layer arranged on the thermal reservoir, the insulating layer comprising an orifice arranged over the LED such that light from the LED passes through the orifice of the insulating layer; and a power source configured to power the LED.

In another aspect, the present disclosure relates to a device comprising: at least one opening, the at least one opening being configured receive an object; an external housing configured to secure to a garment; an entry portion configured to be in a closed state and an open state; a switch disposed on the entrance portion; and an internal housing within the at least one opening, the internal housing comprising: a light emitting diode (LED), a heat sink connecting the LED to the thermal reservoir, and an insulating layer arranged on the thermal reservoir, the insulating layer comprising an orifice arranged over the LED such that light from the LED passes through the orifice of the insulating layer.

In another aspect, the present disclosure relates to device comprising: a light emitting diode (LED); a heat sink connecting the LED to a liquid circulation channel, the heat sink being configured to transfer heat from the LED to the liquid circulation channel; and an insulating layer arranged on the thermal reservoir, the insulating layer including an orifice arranged over the LED such that light from the LED passes through the orifice in the insulating layer.

In further aspects, the present disclosure also relates to garments comprising the disclosed devices.

In still further aspects, the present disclosure also relates to methods for making and using the disclosed systems, devices, and garments. Additional aspects of the present disclosure will be set forth in part in the description which follows, and in part will be obvious from the description, or can be learned by practice of the present disclosure. The advantages of the present disclosure will be realized and attained by means of the elements and combinations particularly pointed out in the appended claims. It is to be understood that both the foregoing general description and the following detailed description are exemplary and explanatory only and are not restrictive of the present disclosure, as claimed.

DETAILED DESCRIPTION

Figure 1:
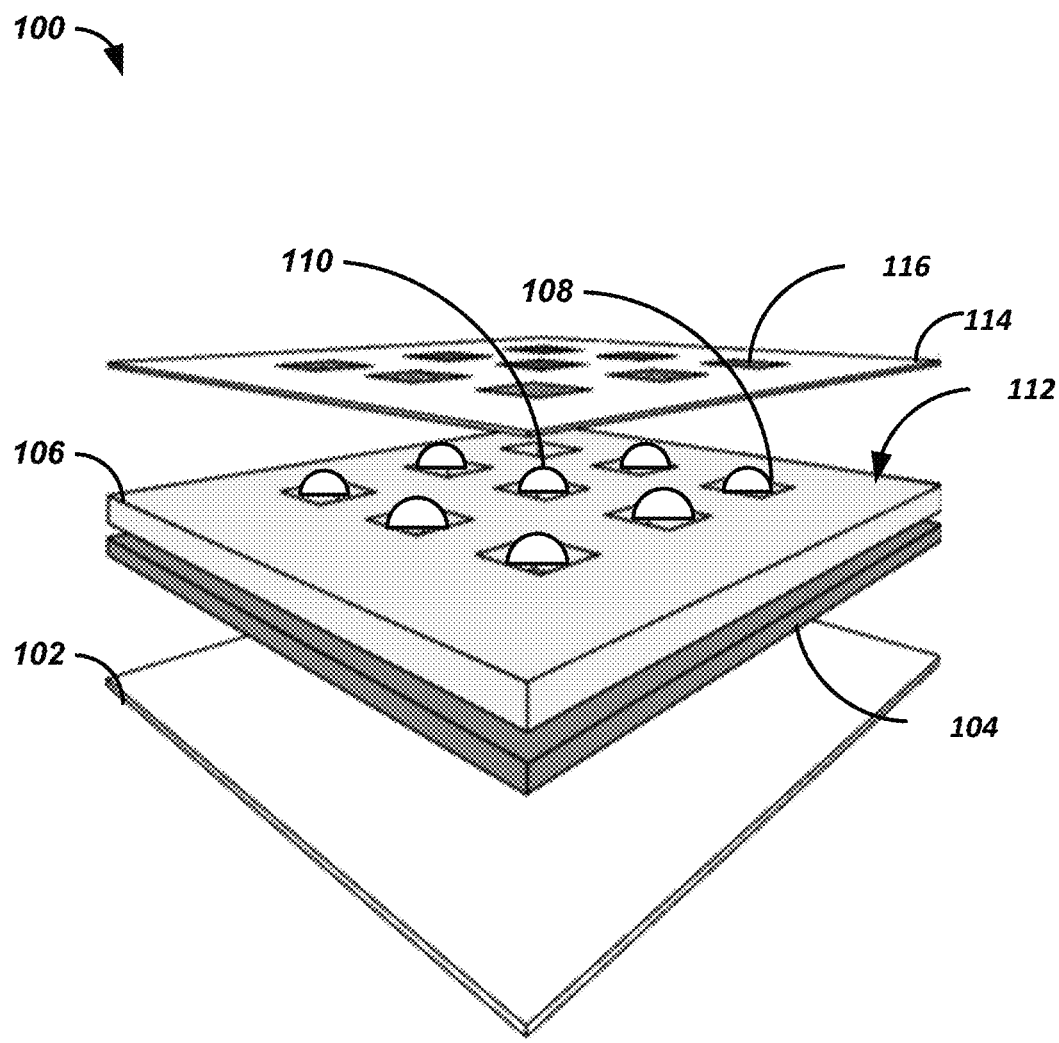
FIG. 1 illustrates an exploded planar view of a flexible disinfecting light device.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subjected matter disclosed under the header.

The present disclosure includes many aspects and features. Moreover, while many aspects and features relate to, and are described in, the context of dispensing fluids, embodiments of the present disclosure are not limited to use only in this context. For example, the principles and techniques disclosed herein may be understood to be applicable for adaptively dispensing other kinds of substances based on associated characteristics.

As discussed above, a portable, quick and effective system for disinfecting hands is desired. In this regard, the use of ultraviolet (UV) lights may be employed to disinfect surfaces. Indeed, UV lights have been found to be effective in disinfecting hands and other surfaces.

UV lights for disinfecting surfaces are often arranged in large fixtures or other devices. These are found in commercial or research settings for disinfecting foods and beverages, hospital rooms, or medical equipment. As discussed above, it is desirable for a system that disinfect hands while being portable and convenient.

The system and devices described herein includes a light emitting diode (LED) array that disinfects the surfaces of objects such as skin of the hands of the user. The device uses LEDs that emit ultraviolet light (and other light frequencies in some embodiments) that disinfects surfaces that it shines upon.

Previous UV disinfection devices were typically fixtures and not portable. Users would place the hands into a compartment with UV light for a period of time. Such a solution is not portable however, and is thus not convenient for most users. Described herein is an apparatus that is portable and emits ultraviolet light to disinfect the hands of the user while the user is undertaking their daily activities.

FIG. 1 illustrates an exploded planar view of a flexible disinfecting light device 100. The device 100 includes a backing cloth 102. The backing cloth 102 may include for example, any number of layers of material including, woven cloth, plastic sheet material, synthetic and natural fiber material. The backing 102 is attached to a thermal reservoir 104.

The thermal reservoir 104 may be deformable and may include any number of channels or cavities that contain a fluid that is operative to disperse heat. The thermal reservoir 104 may connect to the cloth 102 by, for example, stitching, an adhesive or welding process.

The thermal layer (insulating layer) 106 connect to thermal reservoir 104. Thermal layer 106 may include any suitable material such as, for example, neoprene or other similar materials that are flexible, deformable, and are resistant to heat. Thermal layer 106 may include a number of orifices or cavities 108. Cavities 108 may expose LEDs (light emitting devices diodes 110). LEDs 110 in the illustrated embodiment are shown as protruding from the surface 112 of the thermal layer. In other embodiments, the thermal layer 106 may have a thickness that is greater than the height of the LEDs 110 such that the LEDs 110 do not protrude outwardly through the surface 112 of the thermal layer 106. The device 100 may include any number of LEDs 110.

LEDs 110 in the illustrated embodiment may output ultraviolet light or any other light incidental to outputting ultraviolet light. Other embodiments may output light at other wavelengths that has sanitizing or other therapeutic properties.

A top layer 114 may be arranged on the thermal layer 112. Top layer 114 may be formed from any suitable sheet material such as a plastic woven fabric or any other type of suitable synthetic or natural material. Top sheet 114 may comprise a number of orifices that are covered with screen material 116. The orifices generally correspond to the locations of the light emitting diodes 110. Screen material 116 may partially obscure the diodes so as to protect a user from touching warm LEDs 110 while allowing light to pass through the screens 116.

Each of the layers 102, 104, 106, and 114 may be connected together using any suitable method or methods, including for example stitching using adhesives or a welding process.

Figure 2:
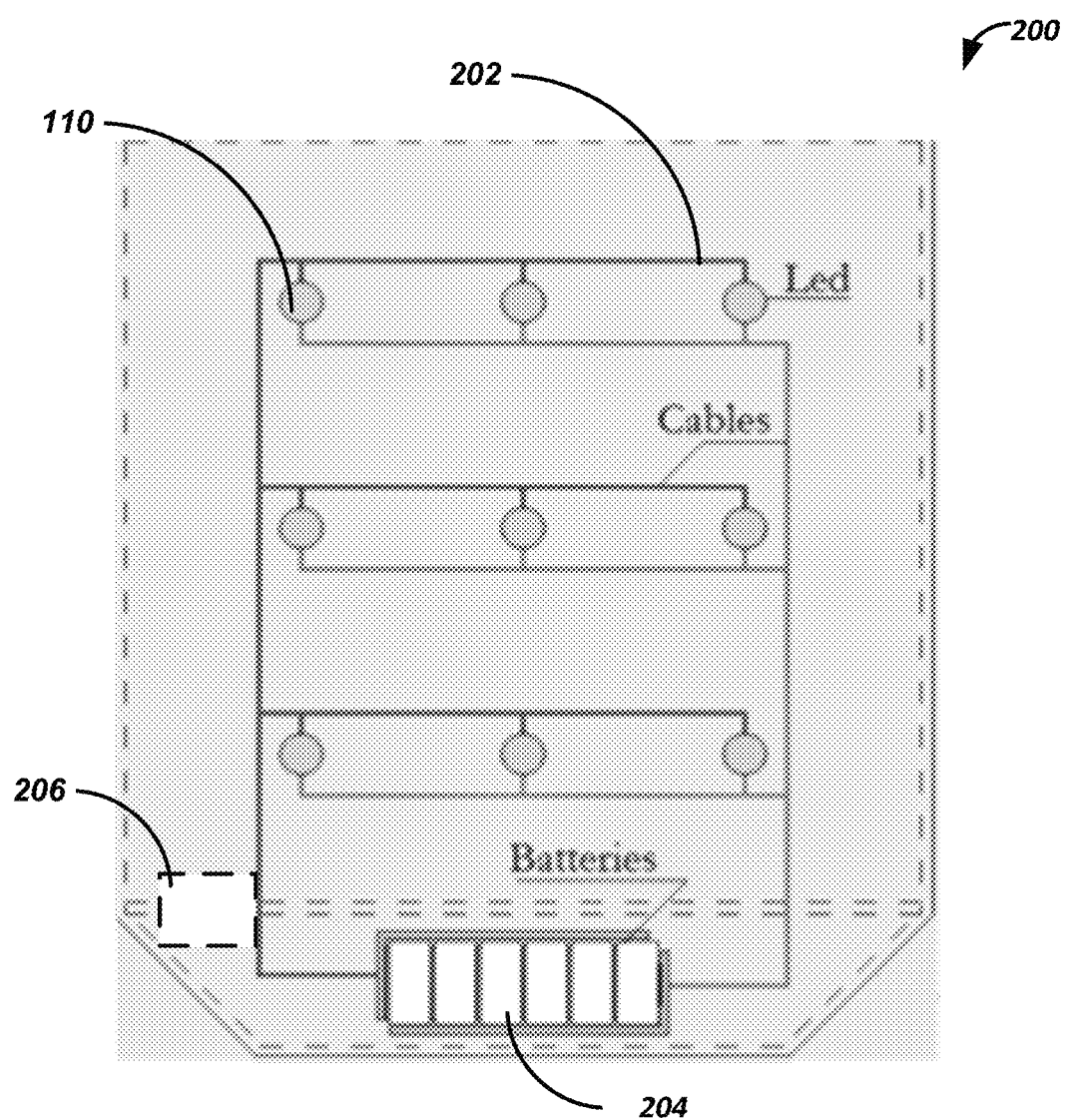
FIG. 2 illustrates a circuit.

FIG. 2 illustrates a circuit 200 that may include light emitting diodes 110, wires 202, and batteries 204 to form the circuit 200. In the illustrated example embodiment, circuit 200 may be an "ideal circuit." Alternative embodiments may comprise controllers and associated circuitry 206 and switches.

Figure 3:
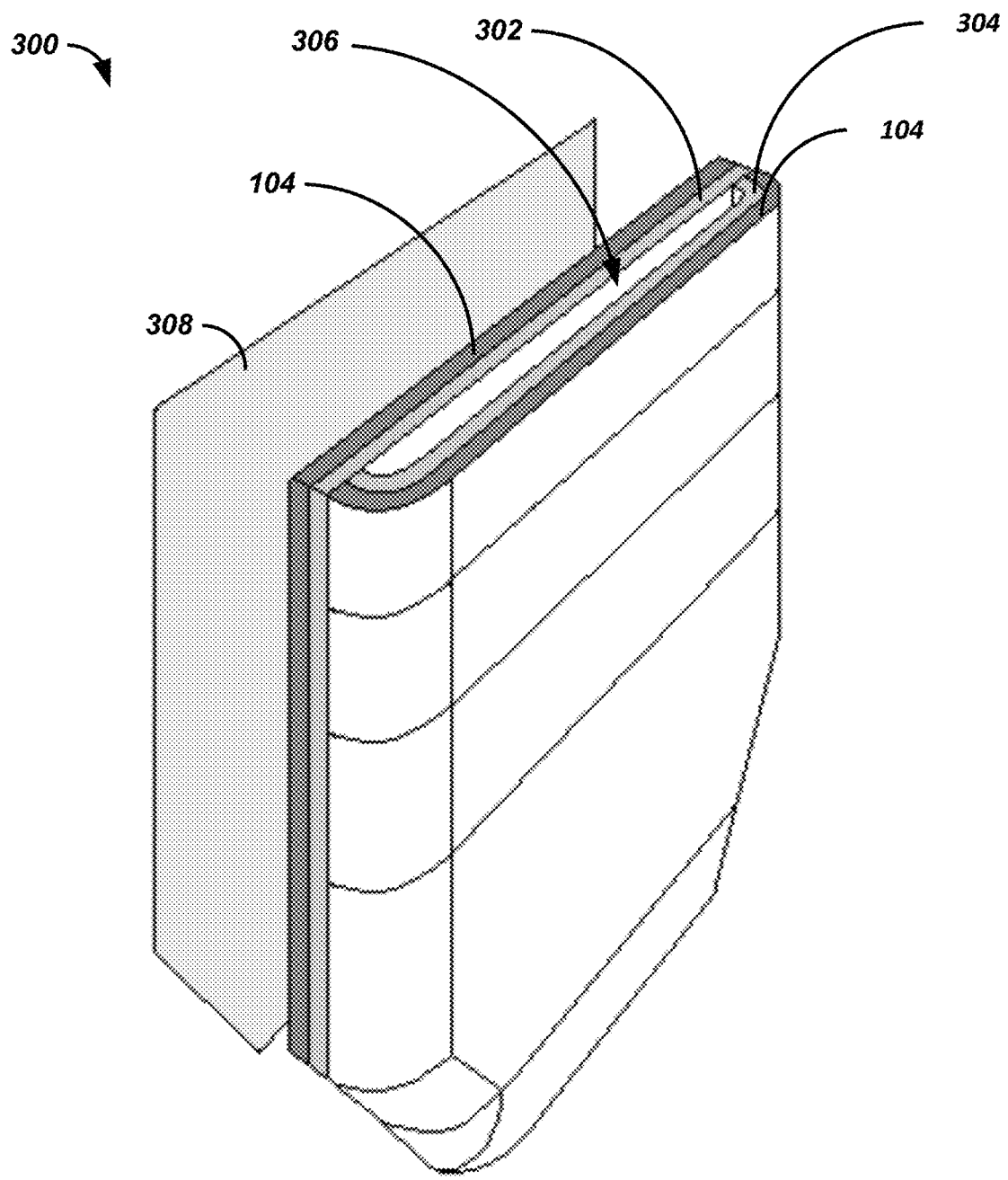
FIG. 3 illustrates a perspective view of an example embodiment of a pocket shaped disinfectant device.

FIG. 3 illustrates a perspective view of an example embodiment of a portion of a pocket shaped disinfectant device 300. The illustrated embodiment may use a first array 302 that is similar to the array 110 of device 100 shown in FIG. 1, and array 304 is also similar to array 110. The array 302 and 304 may be arranged to define a pocket that has an inner cavity 306. A backing layer 308 may be attached to the device 300 to attach the device 300 to a garment or other suitable object.

Interior pocket 306 may be lined with the top sheet 114 (of FIG. 1). LEDs 110 may shine through screen material 112 (of FIG. 1) to illuminate the interior of the pocket and to direct ultraviolet light on opposing sides of the hand of the user.

Figure 4:
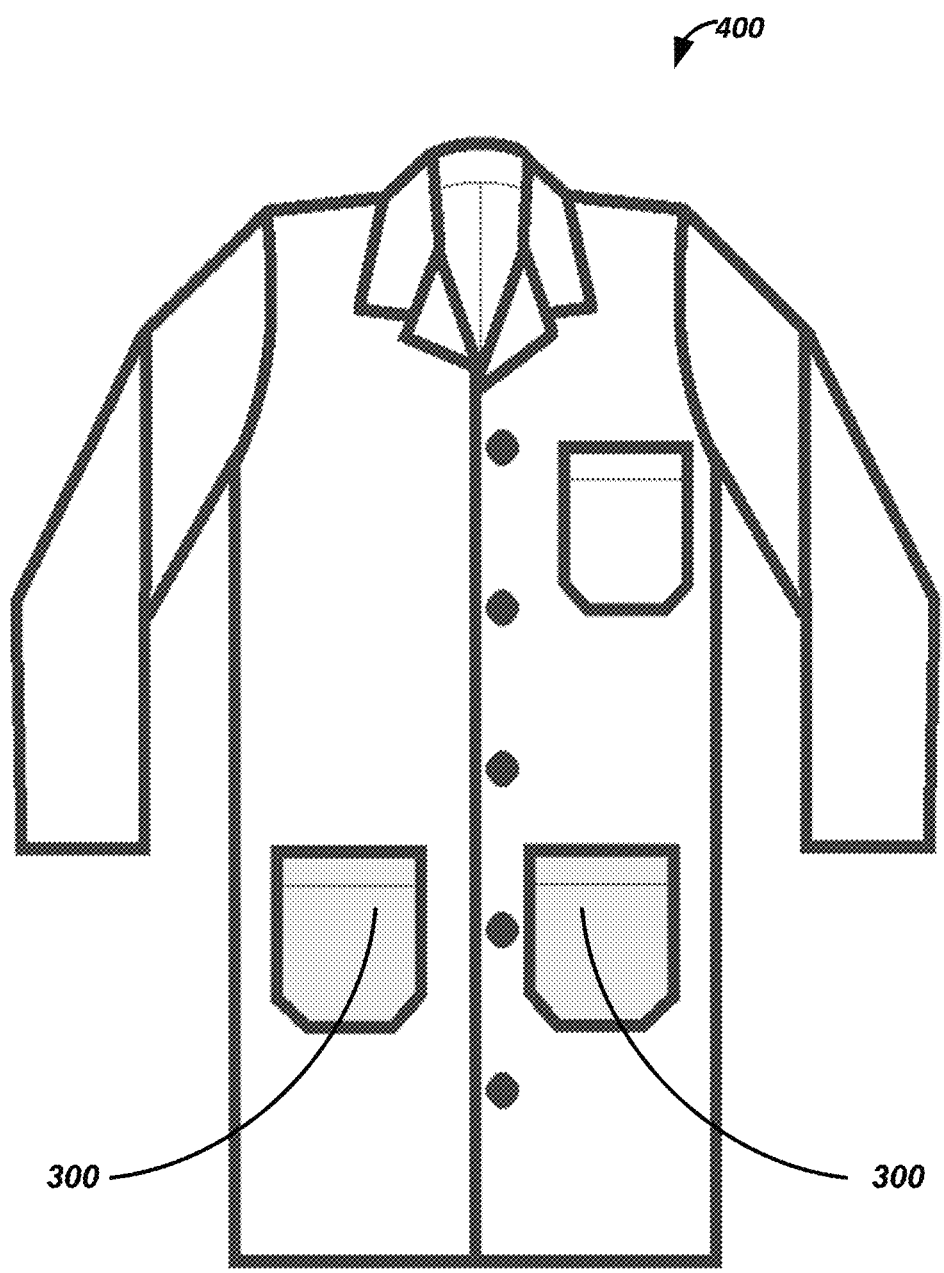
FIG. 4 illustrates a garment that includes the pocket.

FIG. 4 illustrates a garment 400 that includes the pocket shaped device 300. The pocket shaped device 300 may be attached to the garment 400 using any desired attachment component, for example, hook and loop fasteners, stitching, adhesives, snaps, buttons, or other suitable fasteners.

Figure 5:
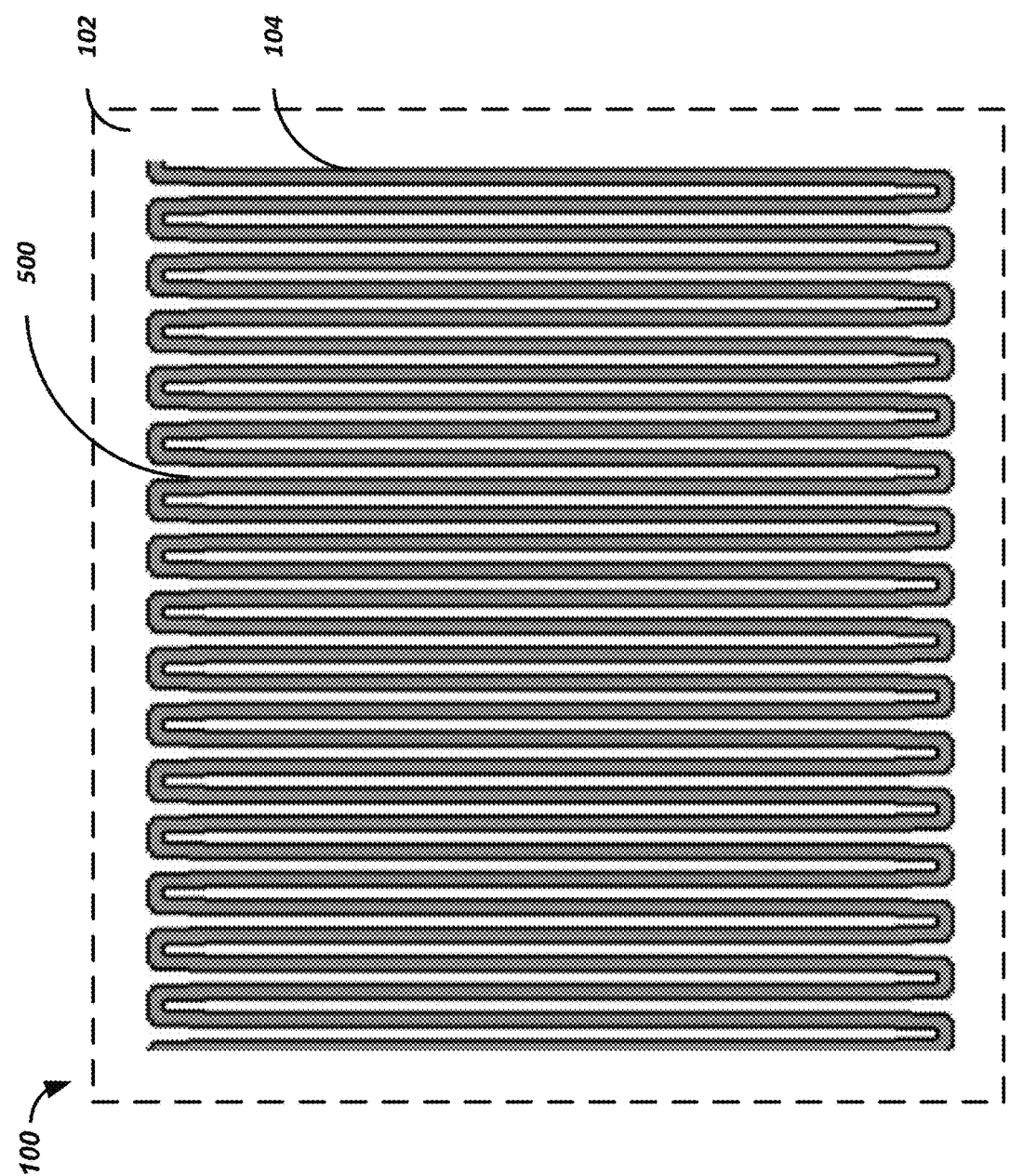
FIG. 5 illustrates the thermal reservoir attached to the backing sheet.

FIGS. 5-8 illustrate a method of manufacturing the device 100. FIG. 5 illustrates thermal reservoir 104 attached to backing sheet 102. Thermal reservoir 104 in the illustrated embodiment may comprise a number of flexible tubes 500 that may be filled with a fluid, such as, for example, water, oil, or other fluid. In various aspects, flexible tubes 500 may comprise cooling channels which may be operative to dissipate heat from LEDs 110.

Figure 6:
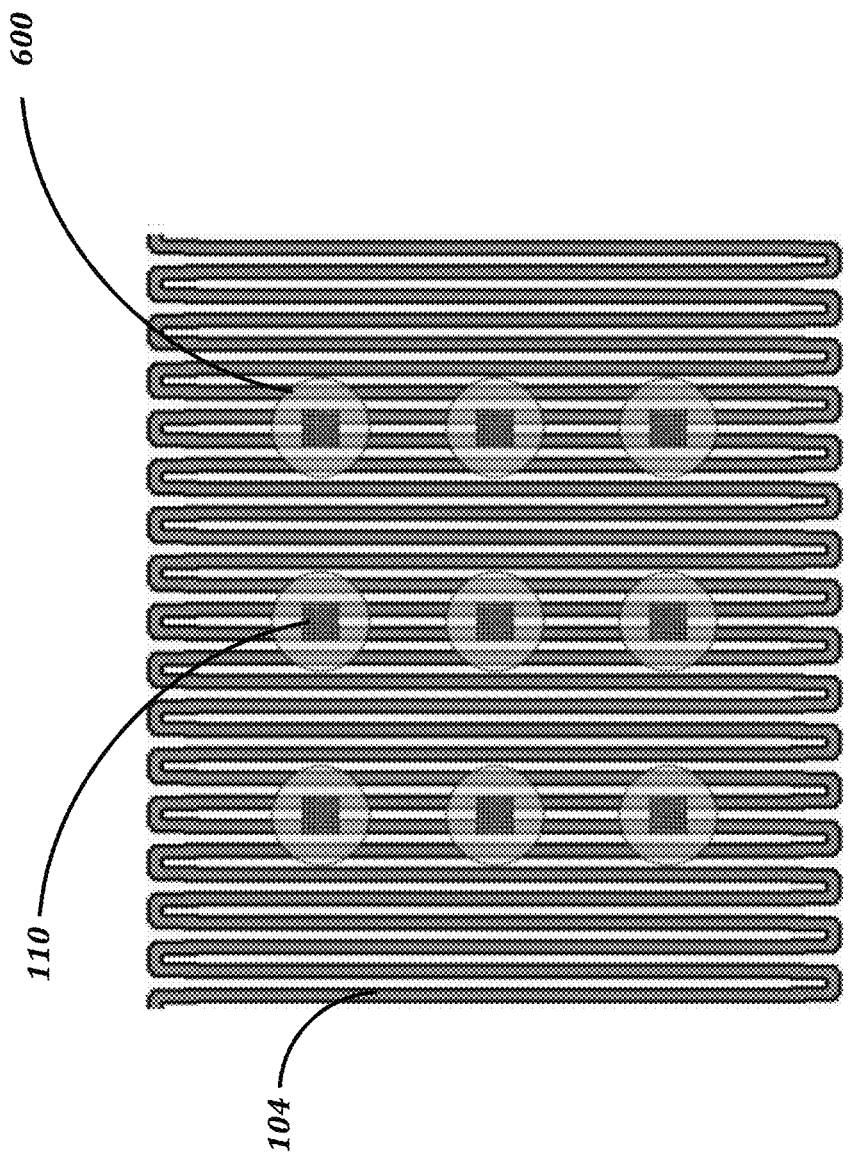
FIG. 6 illustrates a top view of the deposition of LEDs and heatsinks on the reservoir layer.

FIG. 6 illustrates a top view of the deposition of LEDs 110 and heatsinks 600 on the reservoir layer 104. LEDs 110 are connected to the thermal reservoir 104 by heatsinks 600. Heatsinks 600 are operative to conduct heat from the LEDs 110 to the thermal reservoir. Heatsinks 600 may be formed from any suitable material that conducts heat and is substantially flexible, such as, for example, a metallic material such as copper, aluminum, and silver. Heatsinks 600 may be arranged in any suitable shape such as a circular or spiral shape.

Figure 7:
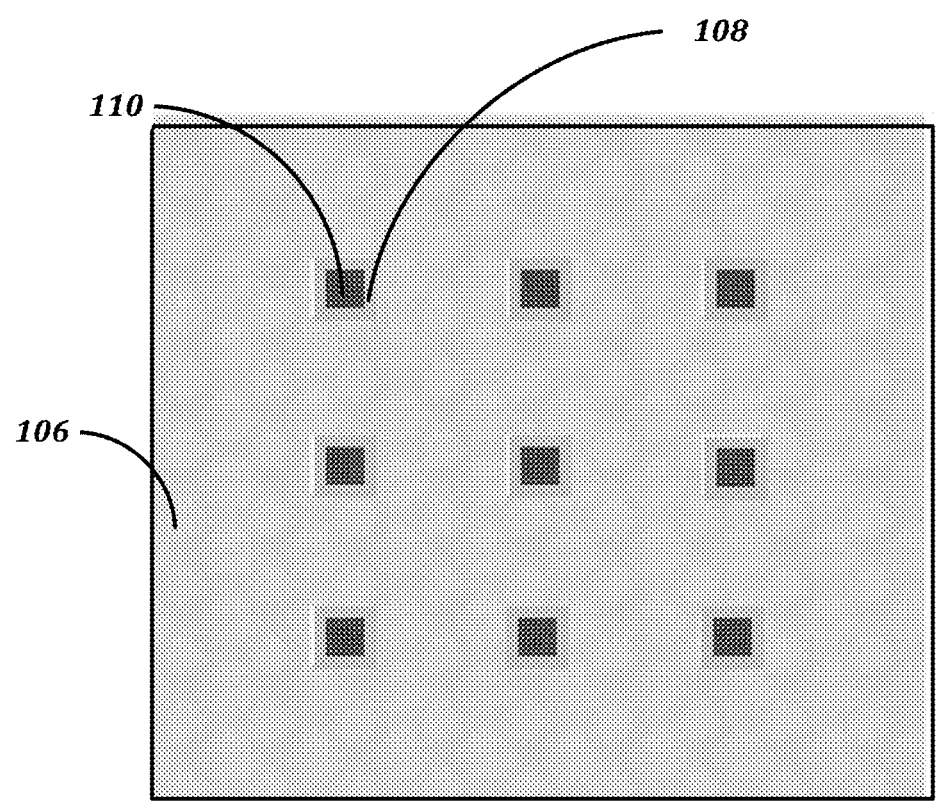
FIG. 7 illustrates a top view of the resulting structure following the arrangement of the thermal (insulating) layer on the heat reservoir.

FIG. 7 illustrates a top view of the resulting structure following the arrangement of thermal (insulating) layer 106 on heat reservoir 104. Portions of LEDs 110 are exposed via orifices 108 in thermal layer 106.

Figure 8:
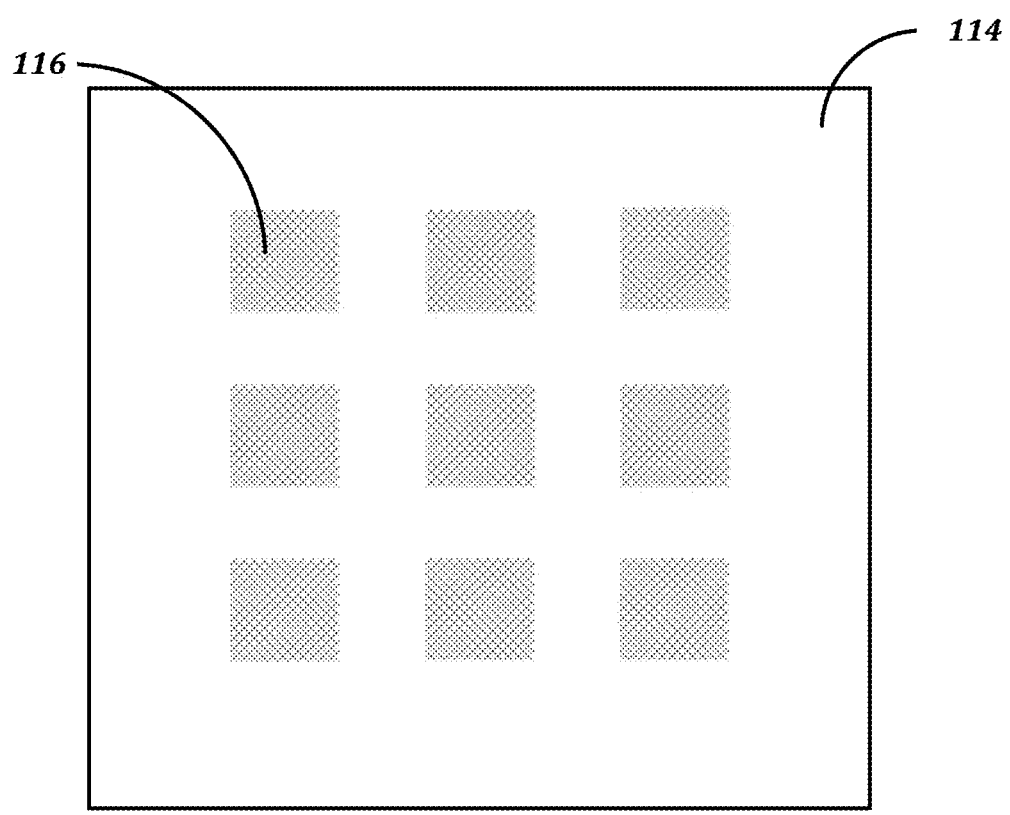
FIG. 8 illustrates a top view of the resulting structure following application of the top layer.

FIG. 8 illustrates a top view of the resulting structure following the application of the top layer 114. Top layer 114 includes screens 116 which protect the user from touching warm LEDs 110 while allowing light to pass through the screens 116 to be emitted into the pocket onto the target surface, such as a user's hand.

Figure 9:
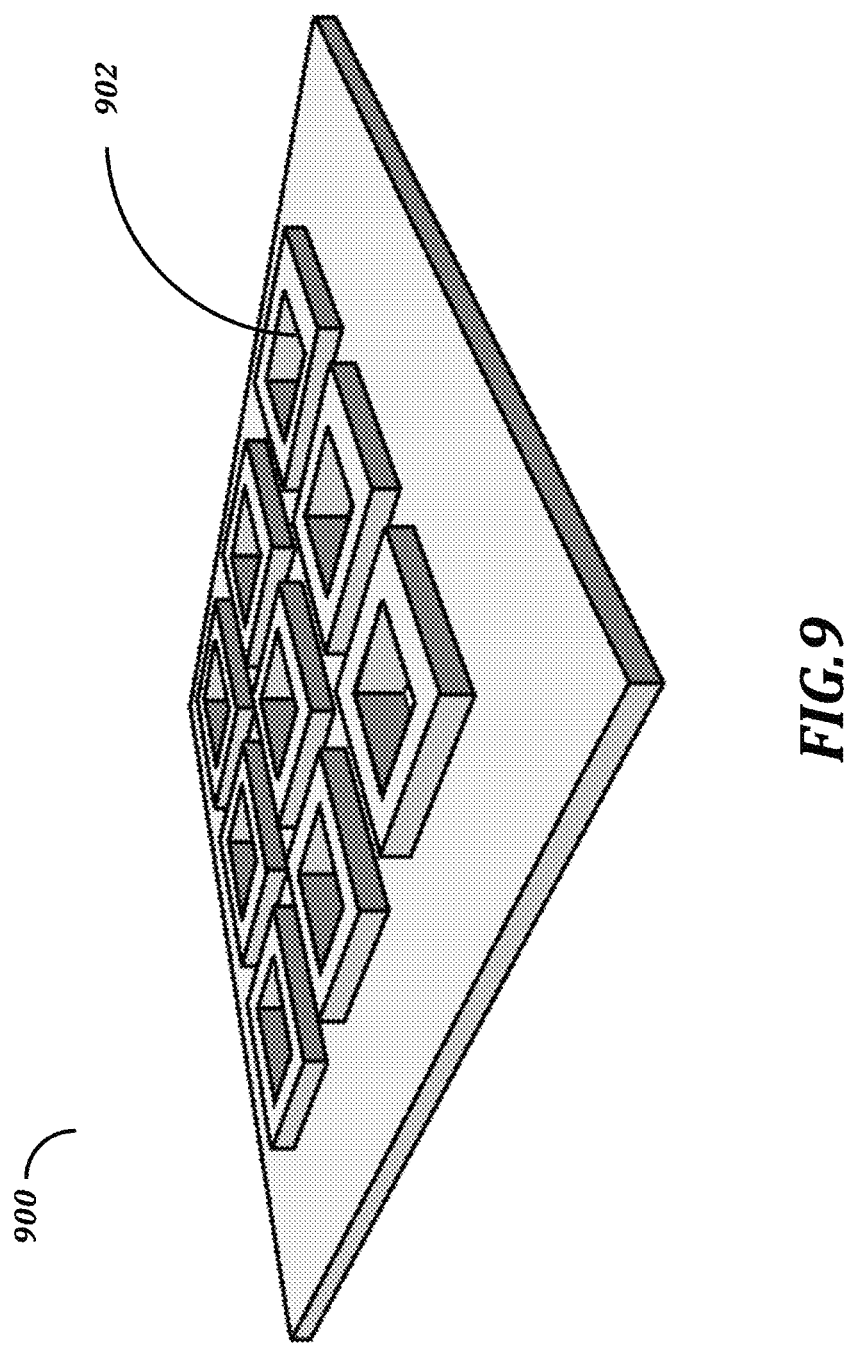
FIG. 9 illustrates a plan view of an alternate embodiment of a thermal layer.

FIG. 9 illustrates a plan view of an alternate embodiment of a thermal layer 900. Thermal layer 900 includes orifices one of the having raised rims 902.

Figures 10, 11, 12:
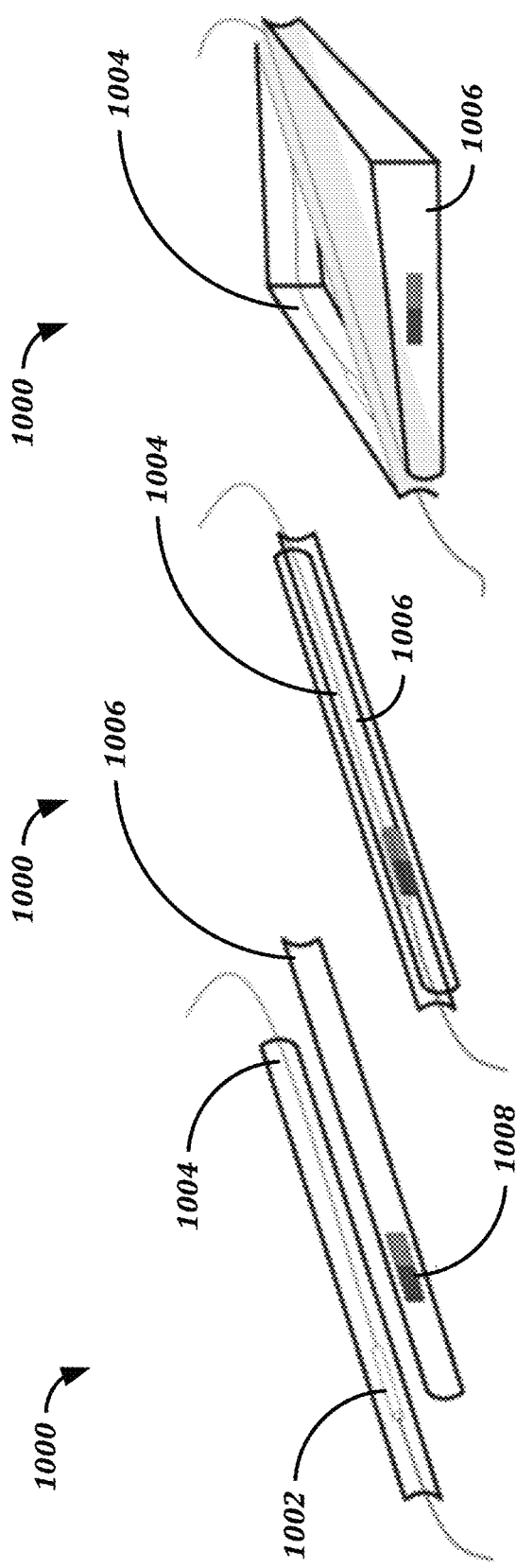
FIG. 10 shows a switch that is attached to a flexible elastic component.
FIG. 11 illustrates the arrangement of the flexible elastic components when set in a substantially parallel position.
FIG. 12 illustrates the flexing deformation of the flexible elastic components.

FIGS. 10-12 illustrate a perspective view of the operation of an example of a switch device 1000 that may be used to operate the pocket device 300 shown in FIG. 3 when placed on opposing sides of the pocket. Switch device 1000 may be arranged proximate to the opening of the pocket such that the switch state is changed when an object such as, for example, a hand enters the pocket.

FIG. 10 illustrates a reed switch 1002 that is attached to a flexible and elastic component like a metal portion 1004. A magnet 1008 is attached to a second flexible and elastic component like a metal portion 1006.

FIG. 11 illustrates the arrangement of flexible metal portions 1004 and 1006 when set in a substantially parallel position. Magnet 1008 is proximate to the reed switch 1002.

FIG. 12 illustrates the flexing deformation of the flexible components, metal pieces 1004 and 1006. The deformation allows the hand of a user to enter into the pocket between the bent flexible components 1004 and 1006 while also separating the reed switch 1002 from magnets 1008. In the illustrated example embodiment, when the reed switch 1002 is separated from magnets 1008, such as when the hand of a user deforms the flexible components 1006, LEDs 110 (of FIG. 1) illuminate the interior of the pocket, such as inner cavity of pocket 306, and the contents of the pocket including the hands of the user.

Figure 13:
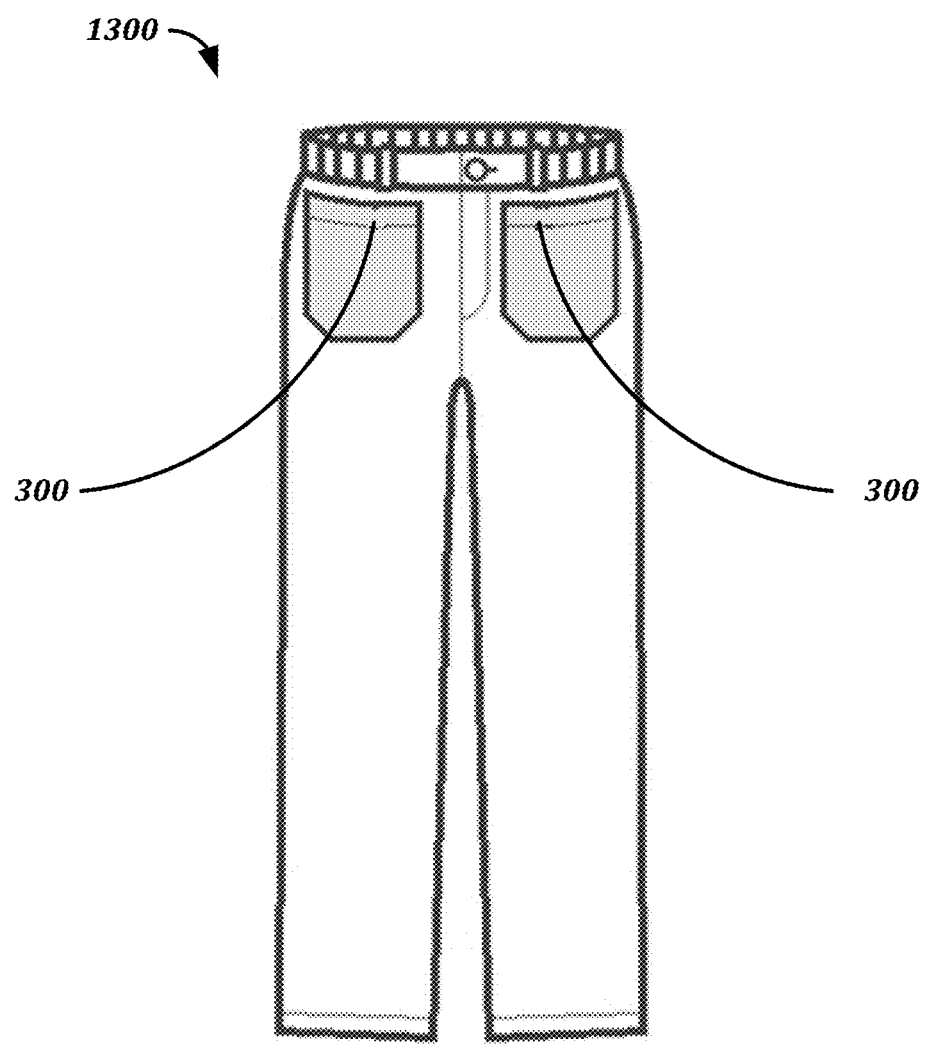
FIG. 13 illustrates an embodiment of a trouser garment.

FIG. 13 illustrates an embodiment of a trouser 1300 garment. The trousers 1300 includes features for receiving and retaining the pocket shaped device 300 such as, for example, hook and loop fasteners, snaps, buttons, or any other suitable attachment arrangement.

Figure 14:
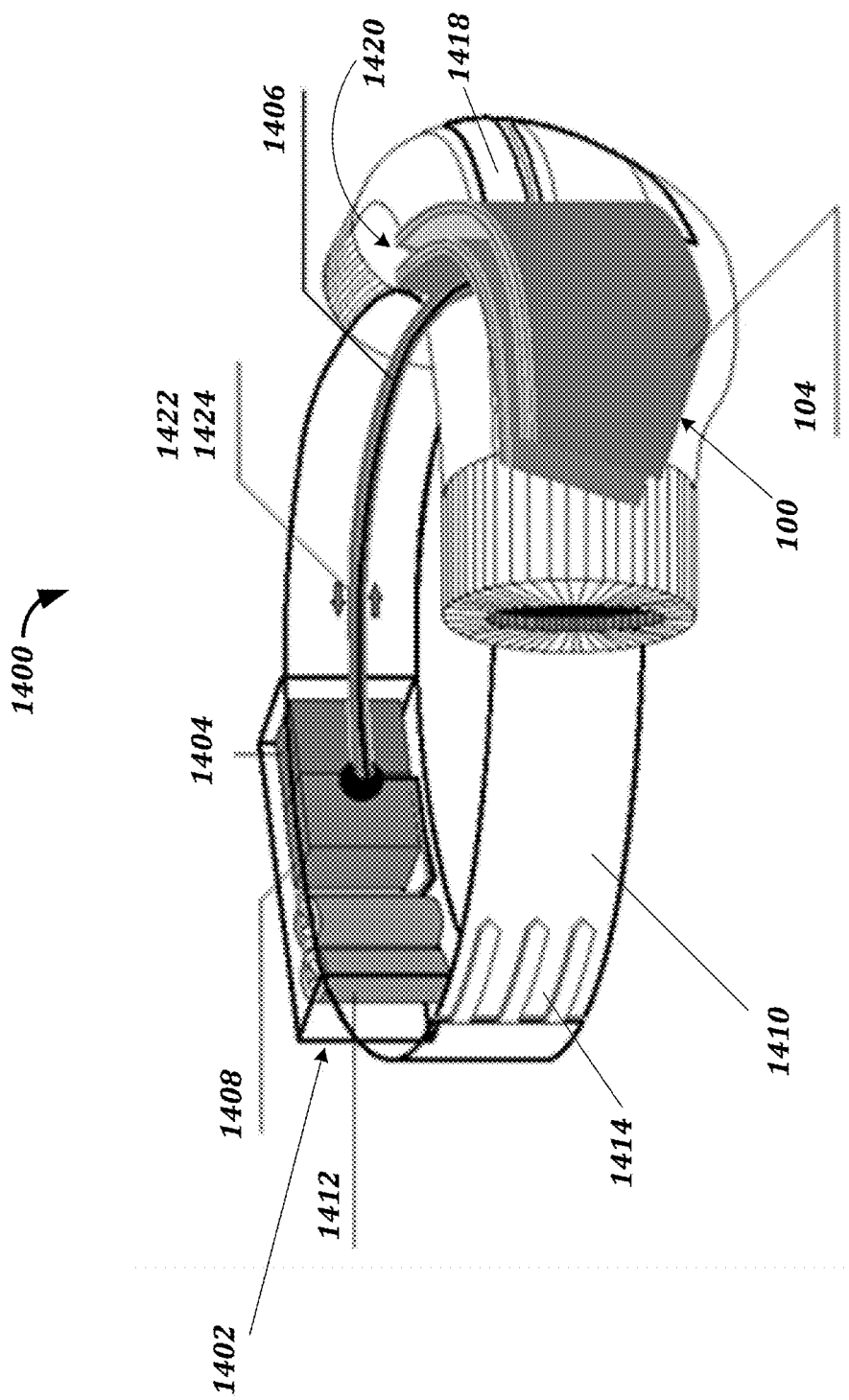
FIG. 14 illustrates a perspective view of an example embodiment of a disinfecting device.

FIG. 14 illustrates an embodiment of a device 1400.

In some embodiments, device 1400 may comprise a liquid exchange portion 1402. In some embodiments, liquid exchange portion 1402 may be configured to connect to a strap portion 1410.

In some embodiments, liquid exchange portion 1402 may comprise a first thermal reservoir 1404. In some embodiments, thermal reservoir 1404 may comprise a number of flexible tubes and/or reservoir that may be filled with a fluid, such as, for example, water, oil, or other fluid.

In further embodiments, liquid exchange portion 1402 may comprise a liquid circulation channel 1406. In some embodiments, liquid circulation channel 1406 may be configured to connect first thermal reservoir 1404 to a second thermal reservoir 104. In further embodiments, liquid circulation channel 1406 may comprise at least one ingress channel 1422 and at least one egress channel 1424. In some aspects, liquid circulation channel 1406 may be contained within strap portion 1410. In other aspects, liquid circulation channel 1406 may be disposed on a surface of strap portion 1410.

In further embodiments, liquid exchange portion 1402 may comprise a liquid pumping device 1408. In some embodiments, liquid pumping device 1408 may be configured to circulate liquid, via liquid circulation channel 1406, between first thermal reservoir 1404 and second thermal reservoir 104.

In further embodiments, liquid exchange portion 1402 may comprise a power source 1412, such as power supply or batteries or the like. In some embodiments, power source 1412 may provide power to device 1400 and components, such as device 100, and/or liquid pumping device 1408.

In further embodiments, device 1400 may comprise strap portion 1410. Strap portion 1410 may be used to secure device 1400 on a user. In some embodiments, strap portion 1410 may comprise a securing means 1414. In further aspects, the securing means may comprise any desired securing mechanism, such as, for example, a cord or strap lock, zipper, buttons, snaps, clips, hooks, fasteners, and combinations thereof.

In further embodiments, device 1400 may comprise a casing or internal housing 1418 configured to contain or house various components of the device. In some embodiments, internal casing 1418 may connect to strap portion 1410. In other embodiments, casing 1418 may be tubular in shape with two opposed opening to allow entry into the interior, such as inserting a hand therein.

In further embodiments, device 1400 may comprise a disinfecting portion 1420. In some embodiments, disinfecting portion 1420 may comprise at least one disinfecting device disclosed herein, for example, device 100 or 300 or a device having a substantially similar configuration. In other embodiments, disinfecting portion 1420 may include a plurality of said devices. In further embodiments, disinfecting portion 1420 may be connect to or otherwise contained within casing 1418. In further embodiments, disinfecting portion 1420 may be arranged to form a pocket. To this end, the interior of said formed pocket is configured to be illuminated by the devices to direct ultraviolet light therein, such as onto opposing sides of the hand of the user when placed inside.

Figure 15:
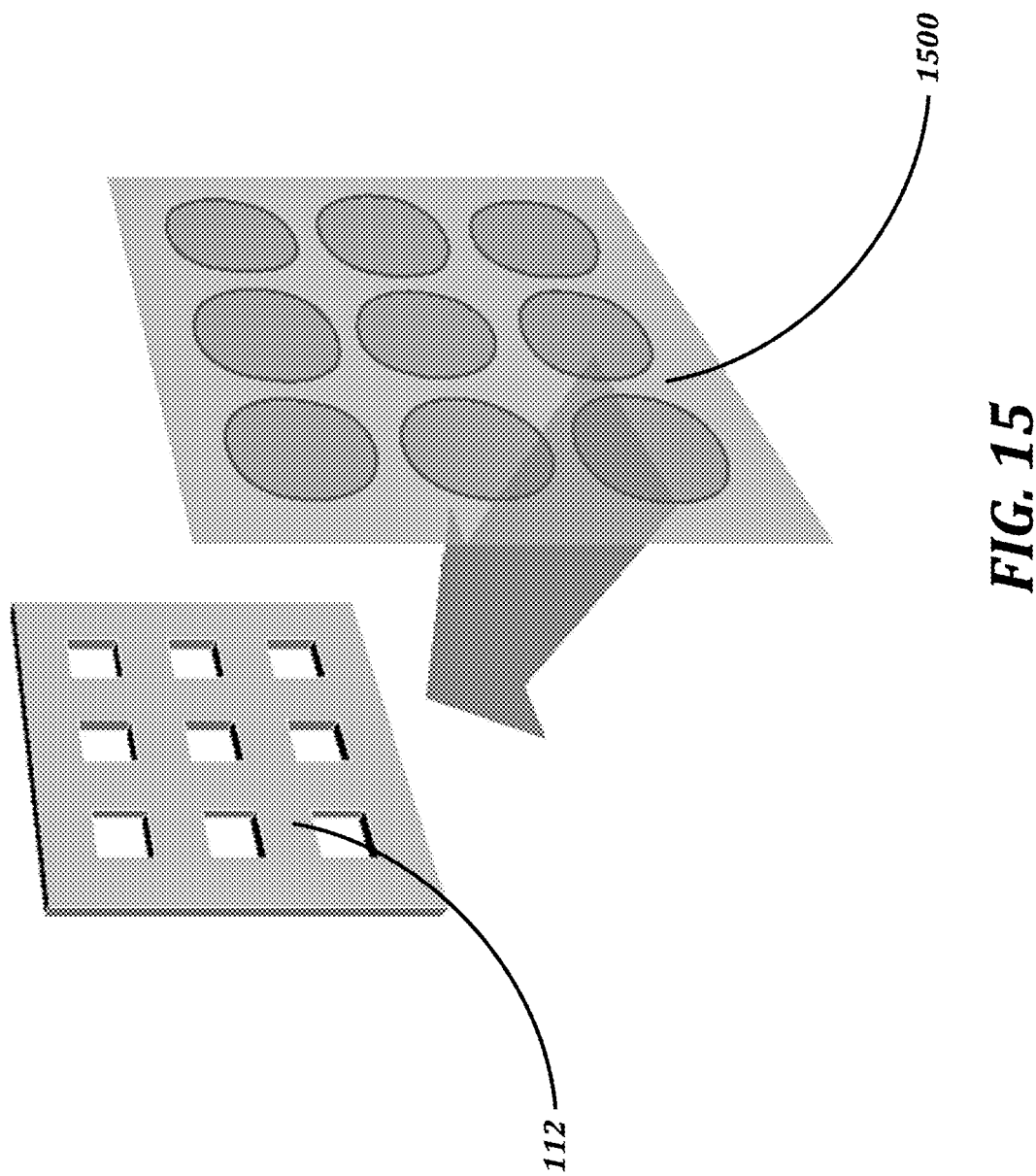
FIG. 15 illustrates an exploded planar view of an alternate top layer.

FIG. 15 illustrates an alternate top layer 1500. In some embodiments, alternate top layer 1500 may be arranged on thermal layer 112. In further embodiments, alternate top layer 1500 may be made from a flexible material. In further embodiments, alternate top layer 1500 may be made from a transparent and/or translucent material. In further embodiments, alternate top layer 1500 may be made from a material capable of passing UV-C light through top layer 1500.

The embodiments described above include a method and device for disinfecting the hands of a user that may be worn as clothing. Such a device can provide a pocket to receive and illuminate the hands of a user with a disinfecting light.

The present disclosure includes at least the following aspects:

Aspect 1: A device comprising: a thermal reservoir; a light emitting diode (LED); a heat sink connecting the LED to the thermal reservoir; and an insulating layer arranged on the thermal reservoir, the insulating layer including an orifice arranged over the LED such that light from the LED passes through the orifice in the insulating layer.

Aspect 2: The device of aspect 1, further comprising a backing layer arranged on the thermal reservoir.

Aspect 3: The device of aspect 1 or 2, further comprising a front layer arranged on the insulating layer.

Aspect 4: The device of aspect 2, wherein the backing layer comprises a fabric.

Aspect 5: The device of aspect 2, 3 or 4, wherein the front layer includes a mesh portion arranged over the orifice.

Aspect 6: The device of any preceding aspect, wherein the LED is operative to emit a light that disinfects when shone on a surface.

Aspect 7: The device of any preceding aspect, wherein the thermal reservoir includes a liquid disposed in a channel.

Aspect 8: The device of any preceding aspect, further comprising a fastener layer arranged on a backing layer.

Aspect 9: The device of any preceding aspect, wherein the insulating layer is deformable.

Aspect 10: The device of any preceding aspect, wherein the thermal reservoir is deformable.

Aspect 11: The device of any preceding aspect, wherein the thermal reservoir layer and the insulating layer are connected by stitching.

Aspect 12: The device of any preceding aspect, wherein the device is actuated by a switch comprising: a first flexible portion; a second flexible portion; and a switch arranged on the first metal portion, the switch operative to change states when the first metal portion is separated from the second metal portion.

Aspect 13: The device of any preceding aspect, arranged to form a pocket.

Aspect 14: The device of aspect 13, wherein the LED is arranged on a first portion of the pocket and a second LED is arranged on a second portion of the pocket that opposes the first portion of the pocket.

Aspect 15: A garment comprising: a pocket having: a thermal reservoir; a light emitting diode (LED); a heat sink connecting the LED to the thermal reservoir; and an insulating layer arranged on the thermal reservoir, the insulating layer including an orifice arranged over the LED such that light from the LED passes through the orifice in the insulating layer.

Aspect 16: The device or garment of aspect 15, further comprising a backing layer arranged on the thermal reservoir.

Aspect 17: The device or garment of aspect 15, further comprising a front layer arranged on the insulating layer.

Aspect 18: The device or garment of aspect 15, wherein the LED is arranged on a first portion of the pocket and a second LED is arranged on a second portion of the pocket that opposes the first portion of the pocket.

Aspect 19: The device or garment of any preceding aspect, wherein the thermal reservoir is deformable.

Aspect 20: A device comprising: a thermal reservoir; a backing layer arranged on the thermal reservoir; a light emitting diode (LED); a heat sink connecting the LED to the thermal reservoir; an insulating layer arranged on the thermal reservoir, the insulating layer including an orifice arranged over the LED such that light from the LED passes through the orifice in the insulating layer; and a front layer arranged on the insulating layer the front layer includes a mesh portion arranged over the orifice.

Aspect 21: A device comprising: a liquid exchange portion comprising: a first thermal reservoir, a liquid circulation channel configured to connect the first thermal reservoir to a second thermal reservoir, and a liquid pumping device configured to circulate liquid, via the liquid circulation channel, between the first thermal reservoir and the second thermal reservoir; and a disinfecting portion configured to disinfect a surface, the disinfecting portion comprising: a light emitting diode (LED), a heat sink connecting the LED to the second thermal reservoir, an insulating layer arranged on the second thermal reservoir, the insulating layer including an orifice arranged over the LED such that light from the LED passes through the orifice of the insulating layer, and a front layer arranged on the insulating layer and over the orifice.

Aspect 22: The device of any preceding aspect, further comprising a backing layer arranged on the second thermal reservoir, wherein the backing layer comprises a fabric.

Aspect 23: The device of any preceding aspect, further comprising a strap portion including a securing means, the strap configured to secure the device to an object or user.

Aspect 24: The device of aspect 23, wherein the liquid exchange portion is configured to connect to the strap portion.

Aspect 25: The device of aspect 23 or 24, further comprising a casing configured to connect to the strap portion.

Aspect 26: The device of aspect 25, wherein the casing is configured to contain the disinfecting portion.

Aspect 27: The device of any preceding aspect, wherein the LED is operative to emit a light effective to disinfect when shone on a surface.

Aspect 28: The device of any preceding aspect, wherein the second thermal reservoir comprises a liquid disposed in a channel.

Aspect 29: The device of any preceding aspect, further comprising a fastener layer arranged on a backing layer.

Aspect 30: The device of any preceding aspect, wherein the second thermal reservoir and the insulating layer are connected by stitching.

Aspect 31: The device of any preceding aspect, wherein the device is activated or actuated by a switch comprising: a first flexible portion; a second flexible portion; and a switch arranged on the first metal portion, the switch operative to change states when the first metal portion is separated from the second metal portion.

Aspect 32: The device of any preceding aspect, wherein the disinfecting portion is arranged to form a pocket.

Aspect 33: The device of any preceding aspect, wherein the LED is arranged on a first portion of a pocket and a second LED is arranged on a second portion of the pocket that opposes the first portion of the pocket.

Aspect 34: The device of any preceding aspect, wherein the liquid circulation channel comprises an ingress channel and an egress channel.

Aspect 35: A garment comprising: a liquid exchange portion comprising: a first thermal reservoir, a liquid circulation channel configured to connect the first thermal reservoir to a second thermal reservoir; a liquid pumping device configured to circulate liquid, via the liquid circulation channel, between the first thermal reservoir and the second thermal reservoir; and a pocket configured to disinfect a surface, the pocket comprising: the second thermal reservoir; a light emitting diode (LED), the LED being operative to emit a light effective to disinfect a surface when shone thereon; a heat sink connecting the LED to the second thermal reservoir; an insulating layer arranged on the second thermal reservoir, the insulating layer including an orifice arranged over the LED such that light from the LED passes through the orifice in the insulating layer; and a front layer arranged on the insulating layer arranged over the orifice.

Aspect 36: The garment of any preceding aspect, further comprising a backing layer arranged on the second thermal reservoir.

Aspect 37: The garment of any preceding aspect, wherein the garment comprises a garment body; wherein the pocket is connected to a first portion of the garment body and the liquid exchange portion is connected to a second portion of the garment body.

Aspect 38: The garment of any preceding aspect, wherein the LED is arranged on a first portion of the pocket and a second LED is arranged on a second portion of the pocket that opposes the first portion of the pocket.

Aspect 39: The garment of any preceding aspect, wherein the second thermal reservoir and the insulating layer are deformable.

Aspect 40: The garment of any preceding aspect, wherein the liquid circulation channel comprises an ingress channel and an egress channel.

Aspect 41: A method for disinfecting an object, the method comprising:
arranging a disinfecting device forming a pocket comprising an inner cavity;
inserting the object inside the inner cavity of the disinfecting device, the disinfecting device comprising:
a light emitting diode (LED);
a heat sink connecting the LED to a thermal reservoir; and
an insulating layer arranged on the thermal reservoir, the insulating layer including an orifice arranged over the LED such that light from the LED passes through the orifice in the insulating layer,
wherein the front layer includes a mesh portion arranged over the orifice; and illuminating the interior of the disinfecting device such that LED shines on the surface of the object.

Aspect 42: The method of any preceding aspect, wherein inserting the object inside the inner cavity of the disinfecting device comprises separating a first flexible portion and a second flexible portion located at an insertion point of the disinfecting device.

Aspect 43: The method of any preceding aspect, wherein separating the first flexible portion and the second flexible portion comprises activating a switch located on the first flexible portion.

Aspect 44: The method of any preceding aspect, wherein inserting the object inside the disinfecting device comprises deforming the inner cavity of the disinfecting device.

Aspect 45: The method of any preceding aspect, further comprising dispersing heat in the thermal reservoir via channels comprised in the thermal reservoir containing fluid.

Aspect 46: The method of any preceding aspect, wherein illuminating, via the LED, the surface of the object comprises directing ultraviolet light on opposing sides of the object Aspect 47: A method for disinfecting an object, the method comprising:
inserting an object inside a disinfecting device;
triggering an activation of the disinfecting device, the activation comprising:
illuminating, via a light emitting diode (LED) passing through at least one orifice of an insulating layer, the interior of the disinfecting device, and
illuminating, via the LED, the surface of the object; and
transferring heat generated from the LED, via a heat sink connected to the LED, to a thermal reservoir Aspect 48: The method of any preceding aspect, wherein inserting the object inside the disinfecting device comprises separating a first flexible portion and a second flexible portion located at an insertion point of the disinfecting device Aspect 49: The method of any preceding aspect, wherein separating the first flexible portion and the second flexible portion comprises activating a switch located on the first flexible portion Aspect 50: The method of any preceding aspect, wherein inserting the object inside the disinfecting device comprises deforming an inner cavity of the disinfecting device Aspect 51: The method of any preceding aspect, further comprising dispersing heat in the thermal reservoir via channels comprised in the thermal reservoir containing fluid Aspect 52: The method of any preceding aspect, wherein illuminating, via the LED, the surface of the object comprises directing ultraviolet light on opposing sides of the object Aspect 53: The method of any preceding aspect, wherein triggering an activation of the disinfecting device comprises activating a power source configured to power the disinfecting device.

Aspect 54: The method of any preceding aspect, further comprising:
orienting the LED on a first portion of the disinfecting device; and
orienting a second LED on a second portion of the disinfecting device that opposes the first portion of the disinfecting device.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way appreciably intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

The patentable scope of the present disclosure is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims.

The following is claimed is:

1. A device comprising:
   at least one opening, the at least one opening being configured receive an object;
   an external housing configured to secure to a garment;
   an inner housing within the at least one opening, the inner housing comprising:
   a light emitting diode (LED),
   a heat sink connecting the LED to a thermal reservoir, and
   an insulating layer arranged on the thermal reservoir, the insulating layer comprising an orifice arranged over the LED such that light from the LED passes through the orifice of the insulating layer; and
   a power source configured to power the LED.

2. The device of claim 1, wherein the at least one opening comprises a switch connected to a first flexible portion and a second flexible portion, the first flexible portion being configured to releasably secure to the second flexible portion.

3. The device of claim 2, wherein the switch is configured to activate the LED upon the first flexible portion being separated from the second flexible portion.

4. The device of claim 1, wherein the thermal reservoir is deformable.

5. The device of claim 1, wherein the LED is arranged on a first portion of the inner housing and a second LED is arranged on a second portion of the inner housing that opposes the first portion of the inner housing.

6. The device of claim 1, further comprising a backing layer arranged on the thermal reservoir.

7. The device of claim 6, further comprising a fastener layer arranged on the backing layer.

8. A device comprising:
   at least one opening, the at least one opening being configured receive an object;
   an external housing configured to secure to a garment;
   an entry portion configured to be in a closed state and an open state;
   a switch disposed on the entry portion; and
   an internal housing within the at least one opening, the internal housing comprising:
   a light emitting diode (LED),
   a heat sink connecting the LED to a thermal reservoir, and
   an insulating layer arranged on the thermal reservoir, the insulating layer comprising an orifice arranged over the LED such that light from the LED passes through the orifice of the insulating layer.

9. The device of claim 8, wherein the entry portion is configured receive the object.

10. The device of claim 8, wherein the device is activated by the switch.

11. The device of claim 8, wherein the switch is operative to change states upon the entry portion being in the open state.

12. The device of claim 8, wherein the LED is arranged on a first portion of internal housing and a second LED is arranged on a second portion of the internal housing that opposes the first portion of the internal housing.

13. The device of claim 8, further comprising a backing layer arranged on the thermal reservoir, wherein the backing layer comprises a fabric.

14. The device of claim 13, further comprising a further comprising a fastener layer arranged on the backing layer.

15. The device of claim 8, wherein the LED is operative to emit light effective to disinfect when shone on a surface.

16. A device comprising:
   an external housing configured to secure to a garment;
   an internal housing formed within an opening configured to receive an object, the internal housing comprising:
   a light emitting diode (LED);
   a heat sink connecting the LED to a liquid circulation channel, the heat sink being configured to transfer heat from the LED to the liquid circulation channel; and
   an insulating layer arranged on a thermal reservoir in communication with the liquid circulation channel, the insulating layer including an orifice arranged over the LED such that light from the LED passes through the orifice in the insulating layer.

17. The device of claim 16, wherein the liquid circulation channel is configured to channel heat away from the heat sink.

18. The device of claim 16, wherein the thermal reservoir and the insulating layer are connected by stitching.

19. The device of claim 16, wherein the liquid circulation channel comprises an ingress channel and an egress channel.

20. The device of claim 16, wherein the liquid circulation channel is deformable.

* * * * *